(12) United States Patent
Nguyen et al.

(10) Patent No.: US 8,475,769 B2
(45) Date of Patent: Jul. 2, 2013

(54) AEROSOL COMPOSITION WITH ENHANCED DISPERSION EFFECTS

(75) Inventors: Peter N. Nguyen, Racine, WI (US); John R. Wietfeldt, Franksville, WI (US); Yemi Susan Bullen, Kenosha, WI (US); Francis J. Randall, Racine, WI (US); Randy C. Yuhas, Union Grove, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 322 days.

(21) Appl. No.: 12/801,792

(22) Filed: Jun. 25, 2010

(65) Prior Publication Data

US 2011/0318276 A1     Dec. 29, 2011

(51) Int. Cl.
*A61K 9/12* (2006.01)
*A61M 11/04* (2006.01)
*B65D 83/00* (2006.01)

(52) U.S. Cl.
USPC ............... 424/45; 424/43; 222/394; 514/958

(58) Field of Classification Search
USPC ................ 424/45, 43; 222/394; 514/958
See application file for complete search history.

(56) References Cited

U.S. PATENT DOCUMENTS

| | | | |
|---|---|---|---|
| 3,102,101 A | 8/1963 | Hawley et al. |
| 3,287,214 A | 11/1966 | Taylor et al. |
| 3,479,297 A | 11/1969 | Rutzen et al. |
| 4,201,764 A | 5/1980 | French et al. |
| 4,439,343 A | 3/1984 | Albanese |
| 4,740,366 A | 4/1988 | Winston et al. |
| 4,826,674 A | 5/1989 | Albanese |
| 4,851,212 A | 7/1989 | Winston et al. |
| 5,209,921 A | 5/1993 | Brobyn et al. |
| 5,516,504 A | 5/1996 | Tomlinson |
| 5,783,544 A | 7/1998 | Trinh et al. |
| 5,800,805 A | 9/1998 | Salas |
| 5,891,427 A | 4/1999 | Mettler |
| 5,919,752 A | 7/1999 | Morelli et al. |
| 5,935,554 A | 8/1999 | Tomlinson |
| 5,939,060 A | 8/1999 | Trinh et al. |
| 6,060,045 A | 5/2000 | Mettler |
| 6,077,318 A | 6/2000 | Trinh et al. |
| 6,077,821 A | 6/2000 | Morelli et al. |
| 6,087,322 A | 7/2000 | Morelli et al. |
| 6,114,302 A | 9/2000 | Morelli et al. |
| 6,133,228 A | 10/2000 | Pika et al. |
| 6,146,621 A | 11/2000 | Trinh et al. |
| 6,199,766 B1 | 3/2001 | Fox et al. |
| 6,218,355 B1 | 4/2001 | Herrmann |
| 6,248,135 B1 | 6/2001 | Trinh et al. |
| 6,279,834 B1 | 8/2001 | Fox et al. |
| 6,369,026 B1 | 4/2002 | Pika et al. |
| 6,451,065 B2 | 9/2002 | Trinh et al. |
| 6,482,357 B1 | 11/2002 | Fox et al. |
| 6,492,323 B2 | 12/2002 | Herrmann |
| 6,592,813 B1 | 7/2003 | Fox et al. |
| 7,018,644 B2 | 3/2006 | Lang |
| 7,182,941 B2 | 2/2007 | Trinh et al. |
| 7,208,465 B2 | 4/2007 | Heltovics et al. |
| 7,638,114 B1 | 12/2009 | Schur et al. |
| 2003/0024997 A1 | 2/2003 | Welch et al. |
| 2003/0096878 A1 | 5/2003 | Harper et al. |
| 2003/0213818 A1 | 11/2003 | Hilvert et al. |
| 2003/0220296 A1 | 11/2003 | Besser et al. |
| 2004/0026462 A1 | 2/2004 | Moshontz et al. |
| 2004/0223871 A1 | 11/2004 | Woo et al. |
| 2004/0223943 A1 | 11/2004 | Woo et al. |
| 2005/0020698 A1 | 1/2005 | Diamond et al. |
| 2005/0037945 A1 | 2/2005 | Gygax et al. |
| 2005/0124512 A1 | 6/2005 | Woo et al. |
| 2005/0152935 A1 | 7/2005 | Lang |
| 2006/0263236 A1 | 11/2006 | Woo et al. |
| 2006/0292111 A1 | 12/2006 | Valpey, III et al. |
| 2007/0098672 A1 | 5/2007 | O'Sullivan |
| 2007/0122373 A1 | 5/2007 | Woo et al. |
| 2007/0134350 A1 | 6/2007 | Higgins et al. |
| 2007/0172382 A1 | 7/2007 | Uchiyama et al. |
| 2007/0231290 A1 | 10/2007 | Robinson et al. |
| 2008/0003193 A1 | 1/2008 | Rebrovic |
| 2008/0193387 A1 | 8/2008 | De Wolff |
| 2008/0248120 A1 | 10/2008 | Anderson et al. |
| 2008/0276523 A1 | 11/2008 | McKechnie |
| 2009/0016966 A1 | 1/2009 | Anson et al. |
| 2009/0130046 A1 | 5/2009 | Clark |
| 2009/0202446 A1 | 8/2009 | Vlad et al. |
| 2009/0325842 A1 | 12/2009 | DeDominicis |

FOREIGN PATENT DOCUMENTS

| | | |
|---|---|---|
| CA | 1106329 | 8/1981 |
| EP | 0 420 538 A1 | 4/1991 |
| EP | 0 897 755 A2 | 2/1999 |
| EP | 1 382 399 A1 | 1/2004 |

(Continued)

OTHER PUBLICATIONS

PCT/US2011/001111 International Search Report dated Sep. 16, 2011.

*Primary Examiner* — Mina Haghighatian

(57) ABSTRACT

A stable, high VOC, single phase, non-aqueous liquid aerosol composition having enhanced dispersion based on reduced particle size and increased evaporation rate to result in improved active ingredient dispersion, slower settling in air and less residue on surfaces. The composition includes at least one hydrocarbon propellant, at least one active ingredient and a solvent blend. The solvent blend includes at least one low volatility solvent and at least one high volatility solvent wherein each has a defined vapor pressure and Hansen solubility parameter. The composition upon dispersion as a spray has an aerosol particle size of less than 30 microns.

17 Claims, No Drawings

FOREIGN PATENT DOCUMENTS

| | | |
|---|---|---|
| EP | 1 884 251 A1 | 2/2008 |
| GB | 2 452 970 A | 3/2009 |
| WO | WO 96/08425 A2 | 3/1996 |
| WO | WO 00/01422 A1 | 1/2000 |
| WO | WO 00/01423 A1 | 1/2000 |
| WO | WO 2006/005007 A1 | 1/2006 |
| WO | WO 2008/047153 A1 | 4/2008 |
| WO | WO 2009/090355 A1 | 7/2009 |

AEROSOL COMPOSITION WITH ENHANCED DISPERSION EFFECTS

FIELD OF INVENTION

An aerosol composition is provided which has an increased evaporation rate and reduced-size aerosol particles which provide for overall enhanced product performance. The smaller particles provide for a greater and longer dispersing of an active compound contained therein (such as a fragrance). The increased evaporation rate reduces the amount of composition which settles on surfaces following spraying of the composition. Enhanced dispersion effects are provided independent of the physical structure of the container and actuator used for dispensing the composition. The composition is especially suitable for use with an automatic electric and/or battery powered dispenser positioned in a static location which sprays a predetermined amount of composition at timed intervals.

BACKGROUND OF INVENTION

Aerosol compositions, such as air fresheners, generally are reliant on the structural design of an actuator cap and/or container to control the particle or droplet size of the composition upon spraying. Smaller particle size on spray application is desirable since smaller particles mean a higher number of particles and greater hang time in the air. Accordingly, since the particles carry the active component of the composition, e.g. a fragrance, this provides for greater dispersion of the active ingredient resulting in a higher intensity of active ingredient for a consumer's benefit.

One problem with aerosol compositions can be in the amount of fall-out or settling on surfaces of the particularized composition. If the settling of the composition particles is too great in quantity, it can result in wetting of surfaces creating slip and fall hazards and/or damage (e.g. to wood surfaces). This is especially a consideration for automatic or timed spraying by an electric or battery powered dispenser which is usually maintained in one location and, accordingly, product spray and consequent fall-out occur in the same location repeatedly at pre-determined intervals over a period of time. Therefore, a reduction in fall-out or settling would be beneficial.

SUMMARY OF INVENTION

An aerosol composition for dispersion of an active ingredient is described which has reduced particle size and an increased evaporation rate based on the composition formulation, not determined by the physical structure of the actuator and container by which the aerosol composition is dispensed, which provides for improved overall product performance. The formulation of the composition provides for particles of less than 30 microns in size. The increase in evaporation rate of volatile components in the composition lead to smaller particle sizes, improved active ingredient delivery, slower settling in the air and less residue from fall-out on surfaces.

The above enhanced composition characteristics are achieved by the provision of a non-aqueous based composition including a solvent blend of low and high volatile solvents having defined solubility parameters. More particularly, an aerosol composition is provided which is a stable single phase non-aqueous liquid aerosol composition for dispersion of an active ingredient into the air including—
   (a) about 20 to about 70 wt. % of at least one hydrocarbon propellant,
   (b) about 0.001 to about 10 wt. % of at least one active ingredient, and
   (c) a solvent blend including
      (i) at least one low volatility solvent having a vapor pressure in a range of from about 0.01 to about 20 mm/Hg at 20° C.,
      (ii) at least one high volatility solvent having a vapor pressure greater than 25 mm/Hg at 20° C., preferably in a range of about 25 to about 500 mm/Hg at 20° C., and
      (iii) optionally, one or more coupling solvents.

The total composition is equal to 100 wt. % and is essentially free of water, i.e., water is not present as an independent ingredient but may be present in another component (e.g. as a carrier) within the composition. Further, the composition upon dispersion has an aerosol particle size of less than 30 microns.

Each component of the solvent blend has a Hansen Solubility Parameter which is used to calculate the solubility parameter "distance" (Ra) between any two solvents where as (1) between each solvent of (i) and each solvent of (ii) above, the Ra is below 20, and (2) when an optional coupling solvent of (iii) is present, each solvent of (i) and of (ii) have a Ra above or below 20 and each solvent of (ii) and each solvent of (iii) have a difference in Ra of below 20, and between each solvent of (i) and each solvent of (iii) above, the difference in Ra is below 20.

The composition before addition of the propellant of (a), which includes the active ingredient(s) of (b) and the solvents of (c), has an average evaporation rate for a first 20% of the composition of greater than 0.03 mg/minute and has an initial evaporation rate for a first 5 wt. % or more of the composition of greater than 0.05 mg/min measured at 50° C.

Active ingredients suitable for use in the aerosol composition include conventional ingredients known for or are suitable for application through dispersion into the air, such as fragrances, odor eliminators, anti-microbials, insecticides, insect repellents, mixtures thereof, and the like.

DETAILED DESCRIPTION OF THE INVENTION

An aerosol composition is provided having certain parameters that enhance product performance. One particular area of improved composition characteristics is the provision of a product having reduced particle or droplet size of the composition upon spray dispensing.

Smaller aerosol particles provide better overall product performance as to the dispersion of the active ingredient(s) contained within the composition and the settling rate of the aerosol particles. The settling rate of the aerosol particles is proportional to the square of particle diameter according to Stoke's Law and therefore smaller particles remain in the air for a longer period of time. This increased residence time in the air has several benefits. Such benefits include (1) the reduction in fall-out or settling upon surfaces which in turn reduces slip and fall hazards, and damage to surfaces due to wetting of the surface; (2) the higher surface area provided by the smaller particles will deliver more active ingredient(s) to the environment in which the composition is applied since the active ingredient(s) is(are) carried in the particles; and (3) provides for improved consumer experience since the smaller particles will be delivered a greater distance away from the exit orifice of an actuator cap which also provides for a greater residency time in the air. The reduced aerosol particle size achieved through the combination of components in the aerosol composition is less than 30 microns, preferably less than 25 microns and most preferably less than 20 microns. The formulation of the aerosol composition as described herein serves to achieve the reduced particle size in absence of a change in actuator cap or valve. However, proper selection of the valve and actuator will serve to maximize the composition break-up on spraying. Two important properties in providing for the reduced particle size are evaporation rate and solubility parameter as to components of the aerosol composition, which are further described below in relation to components of the composition.

The aerosol composition provided is a stable single phase non-aqueous liquid composition which disperses at least one active ingredient contained therein into the air. The aerosol composition includes as components—
  (a) about 20 to about 70 wt. % of at least one hydrocarbon propellant;
  (b) about 0.001 to about 10 wt. % of at least one active ingredient; and
  (c) a solvent blend including
    (i) at least one low volatility solvent having a vapor pressure in a range of from about 0.01 to about 20 mm/Hg at 20° C.;
    (ii) at least one high volatility solvent having a vapor pressure greater than 45 mm/Hg at 20° C.; and
    (iii) optionally, one or more coupling solvents;
  wherein the total composition is equal to 100 wt. % and essentially free or absent of water;
  wherein the composition upon dispersion has an aerosol particle size of less than 30 microns;
  wherein each component of the solvent blend has a Hansen solubility parameter which is used to calculate the solubility parameter distance (Ra) between any two solvents where as (1) between each solvent of (i) and each solvent of (ii) above, the Ra is below 20, and (2) when an optional coupling solvent is present, as between each solvent of (i) and each solvent of (ii), the Ra is above or below 20, and then for each solvent of (ii) and each solvent of (iii) above, the difference in Ra is below 20, and between each solvent of (i) and each solvent of (iii) above, the difference in Ra is below 20; and
  wherein the composition, before addition of the propellant of (a), which includes the active ingredient(s) of (b) and the solvents of (c), has an average evaporation rate for a first 20% of the composition of greater than 0.03 milligrams/minute (mg/min) and has an initial evaporation rate for a first 5 wt. % or more of the composition of greater than 0.05 mg/min measured at 50° C.

As to the propellant component of the aerosol composition, the propellant component is included in an amount of about 20 to about 70 wt. %, preferably about 30 to about 60 wt. %, and most preferably about 45 to about 55 wt. %. Hydrocarbons suitable for inclusion in the composition include lower ($C_1$-$C_4$) aliphatic hydrocarbons such as propane, butane, isopropane, isobutane, and mixtures thereof.

As to the at least one active ingredient of the aerosol composition, such is includable in an amount of about 0.001 to about 10 wt. %, preferably about 1 to about 7 wt. % and most preferably about 2 to about 5 wt. %. One or more active ingredients can be used in combination in the aerosol composition. Active ingredients suitable for inclusion are materials known for or suitable for dispensing through spraying, manually or by aerosol. Examples of active ingredients include fragrances; odor eliminators, such as triethyleneglycol and/or propylene glycol; antimicrobials, anti-bacterials, insecticides, insect repellents, and the like.

The solvent blend provides for the balance of the aerosol composition wherein the total composition is based on 100 wt. %. The total composition is essentially free or absent of water, i.e., water is not present as a separate or independent component of the composition, but may be present as a part of another component of the composition, such as for example as a carrier material.

The solvent blend includes at least (1) one or more of a low volatility solvent having a vapor pressure in a range of from about 0.01 to about 20 mm/Hg at 30° C. and (2) one or more of a high volatility solvent having a vapor pressure greater than 45 mm/Hg at 20° C., more particularly, in a range from about 45 to about 500 mm/Hg at 20° C. A more preferred range for the vapor pressure is from about 75 to about 200 mm/Hg at 20° C. The total amount of low volatility solvent is present in relation to the total amount of high volatility solvent in a ratio of about 3:1 to about 1:3, preferably in a ratio of about 2:1 to about 1:2, and most preferably about 1.5:1 to about 1:1.5, wherein the ratio is based on the wt. % of the low volatility solvent included to the wt. % of the high volatility solvent included in the composition.

The particle size of the aerosol composition upon dispersion as a spray is less than 30 microns, preferably less than 25 microns and most preferably less than 20 microns. Two important properties in achieving the reduced particle size is the evaporation rate of the volatiles contained in the compositions (i.e., solvents, actives, etc.) and the solubility parameters of the solvents.

The evaporation of the volatile components of the aerosol composition leads to smaller particle sizes, improved active ingredient delivery, slower settling in the air (fall-out) and less residue on surfaces. The evaporation rate is defined as the $\Delta$Wt. per minute of a sample material and is best measured in a controlled geometry for components before addition of the propellant of (a), which includes the above ingredient(s) of (b) and the solvents of (c). The evaporation rate of a composition can be measured using a thermal gravimeter analysis instrument (TGA) with a hermetically sealed pinhole lid. The evaporation rate distribution is calculated from the data, i.e., evaporation rate versus the wt. % of the sample that evaporates at that rate, and then determining the differences between the samples. For example, the evaporation of a mass is taken over time, e.g. 100 minutes, at a constant temperature, e.g. 50° C. In using TGA, the wt. % of a sample is taken at the onset of testing and of the liquid sample remaining in the TGA pan as a function of heating time. The more volatile solvents rapidly evaporate and then a slower evaporation rate occurs through a small pinhole in the pan lid of the TGA. The evaporation rate is preferably calculated as mg/minute as a function of wt. % of liquid. The evaporation rate decreases as the material evaporates over time and as the more volatile components of the material are depleted. The evaporation rate can be characterized as the average evaporation rate for the initial 20 wt. % and/or average of some other wt. % of the material. The evaporation rate of the aerosol composition of the invention has an average evaporation rate for the first 20% of the composition of greater than 0.03 mg/min. and has an initial evaporation rate for a first 5 wt. % or more of the composition of greater than 0.05 mg/min measured at 50° C. To provide a standard, it is noted that the evaporation rate for n-butyl acetate using the same procedure is 0.0039 mg/min.

The aerosol composition must be a stable single phase composition to deliver small aerosol particles. The solvents and active ingredient(s), e.g. fragrance(s), are compatible so that phase separation in the composition does not occur as evaporation takes place. This is obtained by the inclusion of solvents having defined solubility parameters. The Hansen Solubility Parameters for each solvent are used to define solvents which are compatible with or dissolve other solvents. The Hansen Solubility Parameters for each solvent are used to calculate the solubility parameter "distance" (Ra) between any two solvents. In practice for determining Ra as to particular materials, solvents are represented as points in a three-dimensional space based on three parameters—D (dispersion), P (polar) and H (hydrogen-bonding). The Hansen Solubility Parameter "distance" (Ra) is defined by—

$$Ra = \text{Square Root}[4(D1-D2)^2 + (P1-P2)^2 + (H1-H2)^2].$$

In the aerosol composition of the invention, each component of the solvent blend has a Hansen Solubility Parameter distance (Ra) of a relationship where as (1) between each solvent of (i) and each solvent of (ii) above, the Ra is below 20, and (2) when an optional coupling solvent is present, the difference between each solvent of (i) and of (ii) is a Ra above or below 20 and then for each solvent of (ii) and each solvent of (iii) above, the difference in Ra is below 20, and between each solvent of (i) and each solvent of (iii) above, the difference in Ra is below 20.

Examples of Hansen Solubility Parameters for certain solvents which are suitable for use in the aerosol composition of the invention are set forth in Table 1 below. Ra values in Table 1 were calculated relative to ISOPAR M.

TABLE 1

| Solvent | Vapor Pressure @ 20° C. (mm/Hg) | D | P | H | Ra |
|---|---|---|---|---|---|
| Acetone | 181.7 | 15.5 | 10.4 | 7 | 12.53794 |
| Ethanol | 44.6 | 15.8 | 8.8 | 19.4 | 21.30634 |
| ISOPAR M | 0.09 | 15.6 | 0 | 0 | |
| ISOPAR L | 0.5 | 14.9 | 0 | 0 | |
| ISOPAR V | 0.1 | | | | |
| Methyl Acetate | 170 | 15.5 | 7.2 | 7.6 | 10.5 |
| Ethyl Acetate | 76 | 15.8 | 5.3 | 7.2 | 8.9 |
| Methyl Ethyl Ketone | 78 | 16.0 | 9.0 | 5.1 | 10.4 |
| Tetrahydrofuran | 143 | 16.8 | 5.7 | 8.0 | 10.1 |

It is noted that Ra was not calculated for low pressure solvents against each other.

The optional coupling solvent(s) may have a low vapor pressure, but has a solubility to aid compatibility of the active ingredient(s) with the low and high volatility solvents. Thus, suitable optional coupling agents are defined as being compatible with the low and high volatility solvents of the solvent blend so as to maintain the active ingredient(s) in solution.

Table 2 below sets forth particle sizes (PS) for different combinations of low vapor pressure solvents and high vapor pressure solvents.

TABLE 2

| Solvent | PS when combined with ISOPAR M (VP = 0.06 mm/Hg @ 20° C.) | PS when combined with ISOPAR L (VP = 1.0 mm/Hg @ 20° C.) | Solvent VP |
|---|---|---|---|
| Acetone | 19.0 | 24.8 | 181.7 |
| Methyl Acetate | 20.9 | 24.4 | 170.0 |
| Tetrahydrofuran | 23.6 | 26.8 | 143.0 |
| Methyl Ethyl Ketone | 22.1 | 24.8 | 78.0 |

Set forth in Table 3 below are intermediate solvent blends suitable for use in the present invention. The blends are shown based on 100 wt. % of the intermediate and are useful in the same proportion in the aerosol composition. Based on wt. % of the total composition, the low volatile solvent is present in the aerosol composition in an amount of about 7 to about 60 wt. %, preferably about 11 to about 48 wt. %. and most preferably about 15 to about 36 wt. %; the high volatile solvent is present in the aerosol composition in an amount of about 7 wt. % to about 60 wt. %, preferably about 11 to about 48 wt. % and most preferably about 15 to about 36 wt. %.

TABLE 3

Intermediate Solvent Blends

| | Solvent Blends | Wt. % |
|---|---|---|
| (1) | ISOPAR V | 57.67 |
| | Acetone | 42.33 |
| (2) | ISOPAR E | 57.67 |
| | Acetone | 42.33 |
| (3) | EXXSOL 95 | 57.67 |
| | Acetone | 42.33 |
| (4) | EXXSOL D3135 Naptha | 57.67 |
| | Acetone | 42.33 |
| (5) | SOLVESSO 150 | 57.67 |
| | Acetone | 42.33 |
| (6) | Butyl Acetate | 57.67 |
| | Acetone | 42.33 |
| (7) | ISOPAR G | 57.67 |
| | Acetone | 42.33 |
| (8) | EXXSOL 130 | 57.67 |
| | Acetone | 42.33 |
| (9) | EXXSOl 60 | 57.67 |
| | Acetone | 42.33 |
| (10) | SOLVESSO 200 | 57.67 |
| | Acetone | 42.33 |
| (11) | SOLVESSO 100 | 57.67 |
| | Acetone | 42.33 |
| (12) | ISOPAR L | 57.67 |
| | Methylpentane Naptha | 42.33 |
| (13) | ISOPAR L | 57.67 |
| | Methyl Acetate | 42.33 |
| (14) | ISOPAR L | 57.67 |
| | 3-Pentanone | 42.33 |
| (15) | ISOPAR L | 57.67 |
| | Ethyl Acetate | 42.33 |
| (16) | ISOPAR L | 57.67 |
| | Propyl Acetate | 42.33 |
| (17) | ISOPAR L | 57.67 |
| | Diethyl Ether | 42.33 |
| (18) | ISOPAR L | 57.67 |
| | Dimethyl Ether | 42.33 |
| (19) | ISOPAR L | 57.67 |
| | Dipropyl Ether | 42.33 |

The intermediate solvent blends of Table 3 illustrate combinations of solvents from different families with varying vapor pressures.

The tradenames are commercial products as follows—

(1) ISOPARC® are high purity isoparaffin fluids with narrow boiling ranges manufactured by ExxonMobil Chemical, wherein differing grades are denoted as E, G, L, M and V;

(2) EXXSOL™ are dearomatized hydrocarbon fluids manufactured by ExxonMobil Chemical; and (3) SOLVESSO™ are aromatic fluids of heavy aromatic grades manufactured by ExxonMobil Chemical. The SOLVESSO™ solvents are also sold under the name "AROMATICS" by ExxonMobil Chemical using the same grade references, e.g. 100, 150 and 200.

Additional hydrocarbon solvents useful in the compositions described herein are sold under the trade name SOLTROL® and made by Chevron Phillips Chemical Company LP. An example of a suitable SOLTROL® grade is SOLTROL® 170 Isoparaffin having as components thereof $C_{12-14}$ Isoalkanes.

EXAMPLES

Set forth below are four examples of high VOC aerosol compositions according to the invention. Each composition includes a fragrance component as the active ingredient and each composition is useful as an air treatment composition. The fragrance component is a fragrance oil of a mixture of hydrocarbons. ISOPAR M, ISOPAR V and ISOPAR L are each an isoparaffin fluid which is a light petroleum distillate manufactured by ExxonMobil Chemical. Propellant A46 is an 80/20 mixture of isobutane/propane, respectively. The ethyl alcohol is 200 Proof (100%).

Example 1

| Ingredient | Wt. % |
| --- | --- |
| ISOPAR M | 30.0 |
| Fragrance | 2.75 |
| Propellant A46 | 40.0 |
| Acetone | 27.25 |

Example 2

| Ingredient | Wt. % |
| --- | --- |
| ISOPAR M | 27.25 |
| Fragrance | 2.75 |
| Propellant A46 | 50.0 |
| Acetone | 20.0 |

Example 3

| Ingredient | Wt. % |
| --- | --- |
| ISOPAR M | 28.0 |
| Fragrance | 2.75 |
| Propellant A46 | 50.0 |
| Ethyl Alcohol | 9.25 |
| Acetone | 10.0 |

Example 4

| Ingredient | Wt. % |
| --- | --- |
| ISOPAR V | 9.0 |
| ISOPAR L | 18.25 |
| Acetone | 20.0 |
| Fragrance | 2.75 |
| Propellant A46 | 50.0 |

Table 4 below shows particle sizes for the compositions of Examples 1, 2, 3 and 4 above, setting forth the mass median diameter (MMD) at the distribution range of 10%, 50% and 90%, as well as the mean value. The tests of Table 4 were conducted using a spray actuator having an exit orifice with a 0.013 inch diameter.

TABLE 4

| Example No. | Fill Wt. | MMD @ 10% | MMD @ 50% | MMD @ 90% |
| --- | --- | --- | --- | --- |
| 1 | 100% | 6.84 | 25.12 | 57.24 |
| 2 | 100% | 5.75 | 19.62 | 47.43 |
| 3 | 100% | 5.33 | 18.13 | 43.81 |
| 4 | 100% | 8.36 | 19.60 | 39.03 |

Table 5 below shows particle sizes for the compositions of Examples 1, 2, 3 and 4 on the same basis as in Table 4 except that the tests were conducted using a spray actuator with an exit orifice having a 0.015 inch diameter.

TABLE 5

| Example No. | Fill Wt. | MMD @ 10% | MMD @ 50% | MMD @ 90% |
| --- | --- | --- | --- | --- |
| 1 | 100% | 6.54 | 24.19 | 58.60 |
| 2 | 100% | 5.32 | 18.45 | 45.40 |
| 3 | 100% | 5.67 | 19.66 | 48.20 |
| 4 | 100% | 5.73 | 18.87 | 38.06 |

Testing was conducted to illustrate the spray performance of various hydrocarbon solvents suitable for use in the compositions described herein. The spray testing set forth in Tables 6 and 7 was conducted with the following base formula:

| Ingredient | Wt. % |
| --- | --- |
| Acetone | 20 |
| Fragrance | 2.75 |
| Propellant A46 | 50 |

The hydrocarbon solvent as noted in Tables 6 and 7 below was present in an amount of 27.25 wt. %. The testing as set forth in Table 8 was conducted based on the formula—

| Ingredient | Wt. % |
| --- | --- |
| Propellant A46 | 50 |
| ISOPAR M | 27.25 |
| High Vapor Pressure Solvent | 20 |
| Fragrance | 2.75 |

The blend of hydrocarbon solvents set forth in Table 9 below is based on the same base formula as set forth above as to Tables 6 and 7, and a blend of 18.25 wt. % and 9 wt. % of solvents as noted in Table 9.

The aerosol test samples were filled into a conventional aerosol container, crimped and pressurized with the propellant. The containers were unlined 211×315 Ball cans with polypropylene laminated (90 μm dose) valves as sold by Seaquist.

Test samples were spray tested using a Malvern analyzer to obtain the Sauter mean diameter (SMD), defined as the ratio of the volume diameter and the surface area diameter, and the mass median diameter (MMD) for a particle diameter wherein 10%, 50% and 90% of the volume sampled is below the measured particle diameter. All test samples were sprayed at 100% full can. All low and high vapor pressure samples of Tables 6-8 were made using the same fragrance. The data results are set forth in Tables 6-9 below for various solvents.

TABLE 6

Spray test results for particle size on low vapor pressure samples

| Sample I.D. | Sample # | Sauter Mean SMD (μm) | MMD 10% (μm) | MMD 50% (μm) | MMD 90% (μm) |
|---|---|---|---|---|---|
| (1) ISOPAR V | 1 | 11.78 | 5.09 | 17.66 | 35.38 |
|  | 2 | 12.09 | 5.20 | 18.00 | 35.89 |
| (2) ISOPAR E | 1 | No Data-Spray bursts were too small for Malvern reading. | | | |
|  | 2 | No Data-Spray bursts were too small for Malvern reading. | | | |
| (3) EXXSOL D95 | 1 | 11.71 | 4.95 | 17.27 | 35.95 |
|  | 2 | 11.53 | 4.96 | 17.22 | 35.65 |
| (4) EXXSOL D3135 Naphtha | 1 | 14.98 | 7.94 | 20.17 | 38.20 |
|  | 2 | 15.20 | 8.14 | 20.60 | 39.00 |
| (5) AROMATIC 150 (SOLVESSO 150) | 1 | 11.45 | 5.67 | 15.30 | 28.57 |
|  | 2 | 11.06 | 5.47 | 15.06 | 28.62 |

TABLE 7

Spray test results for particle size on low vapor pressure samples

| Sample I.D. | Sample # | Sauter Mean SMD (μm) | MMD 10% (μm) | MMD 50% (μm) | MMD 90% (μm) |
|---|---|---|---|---|---|
| (6) ISOPAR G | 1 | 16.23 | 8.58 | 22.05 | 43.80 |
|  | 2 | 16.36 | 8.73 | 22.65 | 45.92 |
| (7) EXXSOL D60 | 1 | 13.66 | 6.50 | 19.30 | 39.98 |
|  | 2 | 14.54 | 6.94 | 20.02 | 39.97 |
| (8) ISOPAR L | 1 | 14.09 | 6.82 | 19.56 | 38.91 |
|  | 2 | 13.10 | 6.82 | 20.61 | 41.59 |
| (9) AROMATIC 200 (SOLVESSO 200) | 1 | 9.58 | 4.73 | 12.61 | 24.60 |
|  | 2 | 9.53 | 4.72 | 12.50 | 24.60 |
| (10) AROMATIC 100 (SOLVESSO 100) | 1 | 14.03 | 7.54 | 18.22 | 32.46 |
|  | 2 | 14.01 | 7.47 | 18.57 | 33.41 |

TABLE 8

Spray test results for particle size on high vapor pressure samples

| Sample I.D. | Sample # | Sauter Mean SMD (μm) | MMD 10% (μm) | MMD 50% (μm) | MMD 90% (μm) |
|---|---|---|---|---|---|
| (11) ISOPAR M & Methyl Acetate | 1 | 11.51 | 5.27 | 16.14 | 32.51 |
|  | 2 | 11.54 | 5.13 | 15.59 | 33.48 |
| (12) ISOPAR M & Ethyl Acetate | 1 | 11.80 | 5.34 | 16.76 | 33.08 |
|  | 2 | 12.35 | 5.55 | 17.70 | 35.57 |
| (13) ISOPAR M & Propyl Acetate | 1 | 15.97 | 8.30 | 19.44 | 38.50 |
|  | 2 | 12.95 | 5.72 | 18.93 | 39.60 |
| (14) ISOPAR M & Diethyl Ether | 1 | 12.13 | 5.56 | 16.99 | 34.32 |
|  | 2 | 12.08 | 5.42 | 17.27 | 35.48 |
| (15) ISOPAR M & 3-Pentanone | 1 | 15.71 | 8.28 | 18.96 | 36.47 |
|  | 2 | 15.71 | 8.33 | 18.88 | 45.56 |
| (16) ISOPAR M & Octyl Acetate | 1 | 15.78 | 7.28 | 22.92 | 45.56 |
|  | 2 | 15.64 | 7.00 | 23.05 | 46.64 |

TABLE 9

Spray test results for particle size on ISOPAR L and ISOPAR V samples at 18.25% and 9%, respectively

| Sample I.D. | Sample # | Sauter Mean SMD (μm) | MMD 10% (μm) | MMD 50% (μm) | MMD 90% (μm) |
|---|---|---|---|---|---|
| (17) ISOPAR L (18.25%) and ISOPAR V (9%) | Fragrance 1 | 16.11 | 8.36 | 19.65 | 39.03 |
| (18) ISOPAR L (18.25%) and ISOPAR V (9%) | Fragrance 2 | 15.76 | 8.35 | 18.94 | 37.10 |
| (19) ISOPAR L (18.25%) and ISOPAR V (9%) | Fragrance 3 | 12.92 | 5.73 | 18.87 | 38.06 |
| (20) ISOPAR L (18.25%) and ISOPAR V (9%) | Fragrance 4 | 12.75 | 5.65 | 18.50 | 37.75 |
| (21) ISOPAR L (18.25%) and ISOPAR V (9%) | Fragrance 5 | 16.09 | 8.34 | 19.63 | 38.58 |
| (22) ISOPAR L (18.25%) and ISOAPR V (9%) | Fragrance 6 | 16.20 | 8.41 | 19.77 | 39.05 |

All test samples at the 50% MMD ranged from about 15 μm to about 23 μm, except for test samples from (9) with AROMATIC 200 (SOLVESSO 200) that measured below 15 μm (12.61 μm and 12.50 μm). The largest particle size measured at 50% MMD was from test sample (16) ISOPAR M & Octyl Acetate at 22.92 μm and 23.05 μm.

Another test was conducted to compare spray performance based on particle size between three commercially sold products and a composition of the invention as set forth below.

Example 5

| Ingredients | Wt. % |
|---|---|
| SOLTROL ® 170 | 27.25 |
| Acetone | 20.0 |
| Fragrance | 2.75 |
| Propellant A46 | 50.0 |

The tests are to illustrate the effect of the actuator on particle size between differing compositions.

The spray testing was conducted using two aerosol samples of each of the composition of Example 5 above, two different air fragrance products sold under the name AIR WICK™ as manufactured by Reckitt Benckiser, and an air fragrance product sold under the name GLADE® as manufactured by S. C. Johnson & Son, Inc. The samples of the invention were filled into unlined 211×315 Ball cans which were then crimped and pressurized with A46 propellant. These samples used a polypropylene laminated (90 μm dose) valve as sold by Seaquist.

Each sample was spray tested using a Malvern analyzer to obtain the mass median diameter (MMD) for a particle diameter which 50% of the volume sampled is below the measured particle diameter. All test samples were sprayed at 100% full can. The actuators from the AIR WICK™ and GLADE® products were interchanged between two samples of each composition tested to show the bearing on the actuator on the spray performance.

TABLE 10

Particle size comparison using AIR WICK ™ and GLADE ® actuators

| Sample | Actuator | 50% MMD (μm) |
|---|---|---|
| AIR WICK ™ #1, Cool Linen & White Lilac | AIR WICK ™ (white) | 29.97 |
| AIR WICK ™ #1, Cool Linen & White Lilac | GLADE ® (black) | 28.12 |
| AIR WICK ™ #2, Fresh Waters | AIR WICK ™ (white) | 30.92 |
| AIR WICK ™ #2, Fresh Waters | GLADE ® (black) | 29.06 |
| GLADE ® #1, Apple Cinnamon | GLADE ® (black) | 19.78 |
| GLADE ® #1, Apple Cinnamon | AIR WICK ™ (white) | 21.25 |
| Example 5 | GLADE ® (black) | 19.51 |
| Example 5 | AIR WICK ™ (white) | 20.02 |

As indicted by the data in Table 10, the particle size did not change significantly when actuators from AIR WICK™ and GLADE® were used on each product. This indicates that the different actuators do not affect particle size, but rather the particle size is dependent on the formula of the composition.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

The invention claimed is:

1. A stable single phase liquid aerosol composition for dispersion of an active ingredient into air comprising
  (a) about 20 to about 70 wt. % of at least one hydrocarbon propellant;
  (b) about 0.001 to about 10 wt. % of at least one active ingredient; and
  (c) a balance of a solvent blend including
    (i) at least one low volatility solvent having a vapor pressure in a range of from about 0.01 to about 20 mm/Hg at 20° C.;
    (ii) at least one high volatility solvent having a vapor pressure in a range greater than 45 mm/Hg at 20° C.; and
    (iii) optionally, one or more coupling solvents;
  wherein the total composition is equal to 100 wt. % and is essentially absent of water;
  wherein the composition has a particle size of less than 30 microns based on formulation of said composition and not by physical structure of an actuator by which the composition is dispensed;
  wherein each component of said solvent blend has a Hansen Solubility Parameter distance (Ra) between any two solvents where as (1) between each solvent of (i) and each solvent of (ii), the Ra is below 20, and (2) when said one or more coupling solvents are present, the difference between each solvent of (i) and each solvent of (ii) is a Ra either above or below 20, and then each solvent of (ii) and each solvent of (iii) have a difference in Ra below 20, and between each solvent of (i) and each solvent of (iii) the difference in Ra is below 20; and
  wherein the composition before addition of said propellant, which includes said at least one active ingredient and said solvent blend, has an average evaporation rate for a first 20 wt. % of said composition of greater than 0.03 mg/min. and has an initial evaporation rate for a first 5 wt. % or more of the composition of greater than 0.05 mg/min measured at 50° C.

2. The composition of claim 1, wherein said at least one low volatility solvent and said at least one high solvent are present in a total amount in relation to each other respectively in a ratio of about 3:1 to about 1:3 based on wt. %.

3. The composition of claim 1, wherein said at least one low volatility solvent is present in an amount of about 7 wt. % to about 60 wt. % and said at least one high volatility solvent is present in an amount of about 7 wt. % to about 60 wt. %.

4. The composition of claim 1, wherein said at least one active ingredient is at least one fragrance.

5. The composition of claim 1, wherein the at least one active ingredient is one or more of a fragrance odor eliminator, antimicrobial, insecticide, insect repellent, and mixtures thereof.

6. The composition of claim 1, wherein said at least one hydrocarbon propellant is at least one $C_1$-$C_4$ hydrocarbon.

7. The composition of claim 1, wherein said propellant is a blend of isobutane and propane.

8. The composition of claim 7, wherein said isobutane is about 80% of said propellant and said propane is about 20% of said propellant.

9. The composition of claim 1, wherein said at least one low volatility solvent is one or more aliphatic hydrocarbons.

10. The composition of claim 9, wherein said one or more aliphatic hydrocarbons is a petroleum distillate.

11. The composition of claim 1, wherein said one or more coupling solvents are present.

12. The composition of claim 11, wherein said one or more coupling solvents comprise one or more of a $C_{1-4}$ alkanol, $C_{1-5}$ ester, $C_{1-6}$ ketone, and $C_{1-4}$ ether.

13. The composition of claim 1, wherein said at least one hydrocarbon propellant is a mixture of isobutane and propane; said at least one active ingredient is one or more fragrances; said solvent blend is composed of acetone, ethanol, and at least one petroleum distillate.

14. The composition of claim 13, wherein said at least one hydrocarbon propellant is present in an amount of about 40 to about 50 wt. %; said at least one active ingredient is present in an amount of about 2 to about 3 wt. %; said at least one petroleum distillate is present in an amount of about 27 to about 28 wt. %; said acetone is present in an amount of about 10 to about 20 wt. %; and said ethanol is present in an amount about 9 to about 20 wt. %.

15. A liquid composition for dispersion of an active ingredient into air, wherein said composition
  (a) is a stable single phase;
  (b) includes at least one hydrocarbon propellant, a solvent blend and at least one active ingredient; wherein said solvent blend is (i) at least one aliphatic hydrocarbon, (ii) acetone and (iii) optionally, a $C_{1-4}$ alkanol; and
  (c) said composition has an aerosol particle size of less than 30 microns based on formulation of said composition and not by physical structure of an actuator by which the composition is dispensed;
  wherein each component of said solvent blend has a Hansen Solubility Parameter distance (Ra) of (1) between each solvent of (i) and each solvent of (ii), the Ra is below 20, (2) between each solvent of (ii) and each solvent of (iii) the difference in Ra is below 20, and (3) between each solvent of (i) and each solvent of (iii) the difference in Ra is below 20;

wherein the composition, before addition of said propellant, which includes said at least one active ingredient and said solvent blend, has an average evaporation rate for a first 20 wt. % of said composition of greater than 0.03 mg/min. and has an initial evaporation rate for a first 5 wt. % or more of the composition of greater than 0.05 mg/min. measured at 50° C.; and wherein said composition in total is present in an amount of 100 wt. %.

16. A liquid composition for dispersion of an active ingredient into air, wherein said composition (a) is a stable single phase;

(b) includes at least one hydrocarbon propellant, a solvent blend and at least one fragrance; wherein said solvent blend is at least one aliphatic hydrocarbon, acetone and, optionally, ethanol; and (c) said composition has an aerosol particle size of less than 30 microns based on formulation of said composition and not by physical structure of an actuator by which the composition is dispensed;

wherein each component of said solvent blend has a Hansen Solubility Parameter distance (Ra) where as (1) between each of said at least one aliphatic hydrocarbon and said acetone the Ra is below 20, and (2) between each of said at least one aliphatic hydrocarbon and said ethanol there is a difference in Ra of below 20;

wherein the composition, before addition of the propellant, which includes said fragrance and said solvent blend, has an average evaporation rate for a first 20 wt. % of said composition of greater than 0.03 mg/min. and has an initial evaporation rate for a first 5 wt. % or more of the composition of greater than 0.05 mg/min.; and wherein said composition in total is present in an amount of 100 wt. %.

17. The composition of claim 16, wherein said ethanol is present.

* * * * *